US012687553B2

(12) United States Patent
Follet et al.

(10) Patent No.: US 12,687,553 B2
(45) Date of Patent: Jul. 21, 2026

(54) METHOD FOR CAPTURING AND IDENTIFYING CELLULAR AGGLUTINATES FOR DETECTING MULTIPLEX ANTI-ERYTHROCYTE ANTIBODIES

(71) Applicant: INNOBIOCHIPS, Loos (FR)

(72) Inventors: Pauline Follet, Rexpoede (FR); Pierre Lebrun, Meurchin (FR); Christophe Olivier, Libercourt (FR); David Poirier, Laval (FR); Vianney Souplet, Quesnoy sur Deule (FR)

(73) Assignee: INNOBIOCHIPS, Loos (FR)

( * ) Notice: Subject to any disclaimer, the term of this patent is extended or adjusted under 35 U.S.C. 154(b) by 904 days.

(21) Appl. No.: 17/760,021

(22) PCT Filed: Feb. 4, 2021

(86) PCT No.: PCT/EP2021/052712
§ 371 (c)(1),
(2) Date: Aug. 3, 2022

(87) PCT Pub. No.: WO2021/156391
PCT Pub. Date: Aug. 12, 2021

(65) Prior Publication Data
US 2023/0062669 A1 Mar. 2, 2023

(30) Foreign Application Priority Data
Feb. 4, 2020 (FR) ...................................... 2001091

(51) Int. Cl.
*G01N 33/80* (2006.01)
*G01N 33/577* (2006.01)
(52) U.S. Cl.
CPC ........... *G01N 33/80* (2013.01); *G01N 33/577* (2013.01); *G01N 2400/10* (2013.01)

(58) Field of Classification Search
None
See application file for complete search history.

(56) References Cited

U.S. PATENT DOCUMENTS

2007/0077605 A1 4/2007 Hurt et al.
2010/0178656 A1* 7/2010 Buffiere ........... G01N 33/54333
435/7.1

(Continued)

FOREIGN PATENT DOCUMENTS

EP 0 223 978 A1 6/1987
FR 2917174 A1 12/2008

(Continued)

OTHER PUBLICATIONS

Uno et al: "Sensitive typing of reverse ABO blood groups with a waveguide-mode sensor", Journal of Bioscience and Bioengineering, vol. 126, No. 1, p. 131-137, Feb. 28, 2018.

(Continued)

*Primary Examiner* — Rebecca M Giere
(74) *Attorney, Agent, or Firm* — WCF IP

(57) ABSTRACT

The present invention relates to an in-vitro method for detecting anti-erythrocyte antibodies in a sample, comprising at least the following steps: a) bringing the sample into contact with one or more test erythrocytes or a suspension of one or more test erythrocytes having a known phenotype, under conditions likely to induce hemagglutination, so as to obtain a reaction mixture; b) bringing the reaction mixture into contact with a solid substrate containing a plurality of defined adsorption areas which have previously fixed antibodies or antibody fragments capable of binding antigenic determinants present on the one or more test erythrocytes; c) ascertaining the presence or absence of a hemagglutination reaction in at least one of the adsorption areas so as to detect the presence or absence of anti-erythrocyte antibodies in the (Continued)

Capture antibody imprinted on the surface
Microtitration plate well bottom
Agglutinated test red blood cells
Antibody causing agglutination
Non-agglutinated test red blood cells Plasma to be tested + test red blood cells sample; the steps a) and b) being carried out separately or simultaneously.

15 Claims, 3 Drawing Sheets

(56)                    References Cited

U.S. PATENT DOCUMENTS

2010/0184102  A1*    7/2010   Chaibi  ................... G01N 33/80
                                                                            435/7.25
2013/0203629  A1*    8/2013   Melnyk ............ G01N 33/54393
                                                                            536/55.1

FOREIGN PATENT DOCUMENTS

| | | | |
|---|---|---|---|
| FR | 2918460 | A1 | 1/2009 |
| FR | 2966248 | A1 | 4/2012 |
| JP | 2010271282 | A | 12/2010 |
| JP | 2013545971 | A | 12/2013 |
| WO | 1985/001354 | A1 | 3/1985 |
| WO | 2002/016942 | A1 | 2/2002 |
| WO | 2006/100477 | A1 | 9/2006 |
| WO | 2007/051844 | A1 | 5/2007 |
| WO | 2008/148886 | A1 | 12/2008 |
| WO | 2009/007649 | A2 | 1/2009 |
| WO | 2012/010666 | A1 | 1/2012 |
| WO | 2019/158726 | A1 | 8/2019 |

OTHER PUBLICATIONS

Japanese Office Action dated Dec. 10, 2024.

* cited by examiner

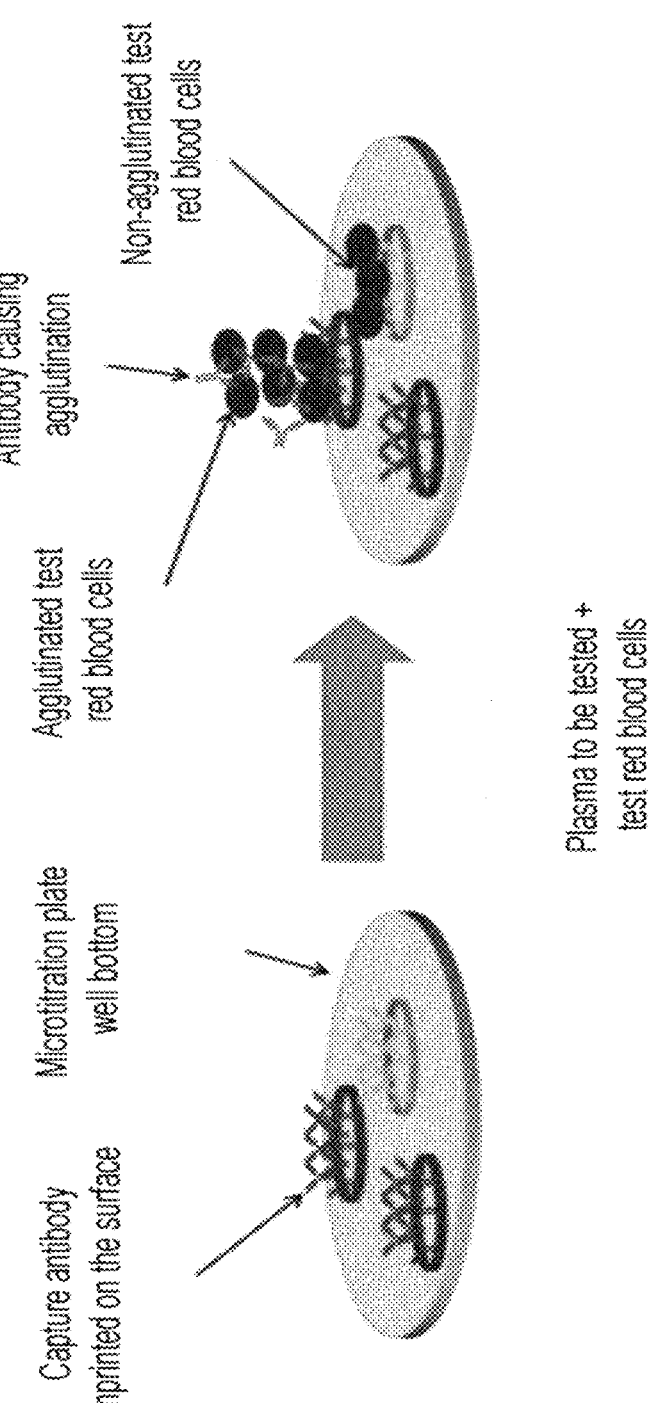
[Fig 1]

[Fig 2]
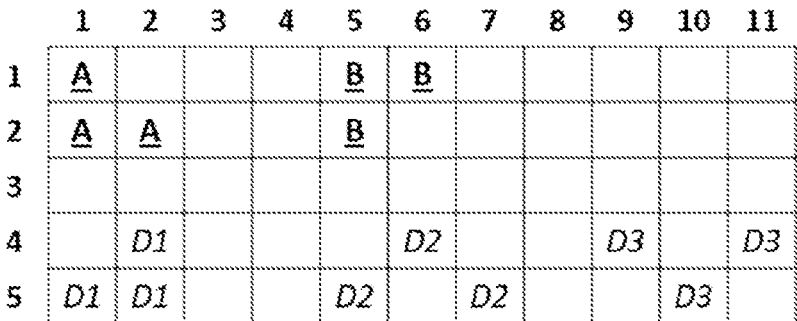
|   | 1 | 2 | 3 | 4 | 5 | 6 | 7 | 8 | 9 | 10 | 11 |
|---|---|---|---|---|---|---|---|---|---|----|----|
| 1 | A |   |   |   | B | B |   |   |   |    |    |
| 2 | A | A |   |   | B |   |   |   |   |    |    |
| 3 |   |   |   |   |   |   |   |   |   |    |    |
| 4 |   | D1 |   |   |   | D2 |   |   | D3 |   | D3 |
| 5 | D1 | D1 |   |   | D2 |   | D2 |   |   | D3 |    |
Simonin & *RAI*
[Fig 3]
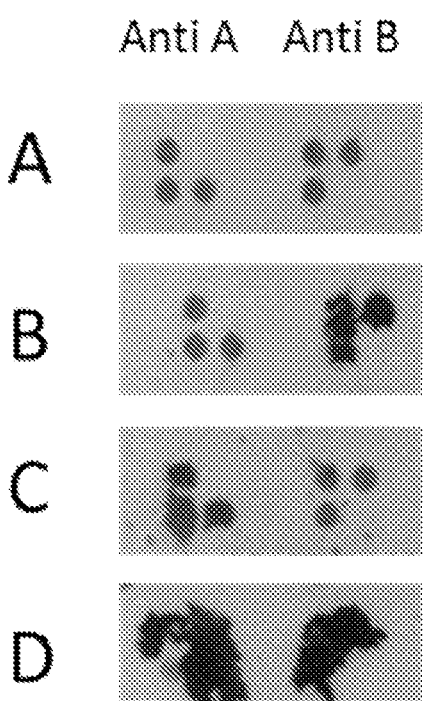
Anti A    Anti B
A
B
C
D

[Fig 4]
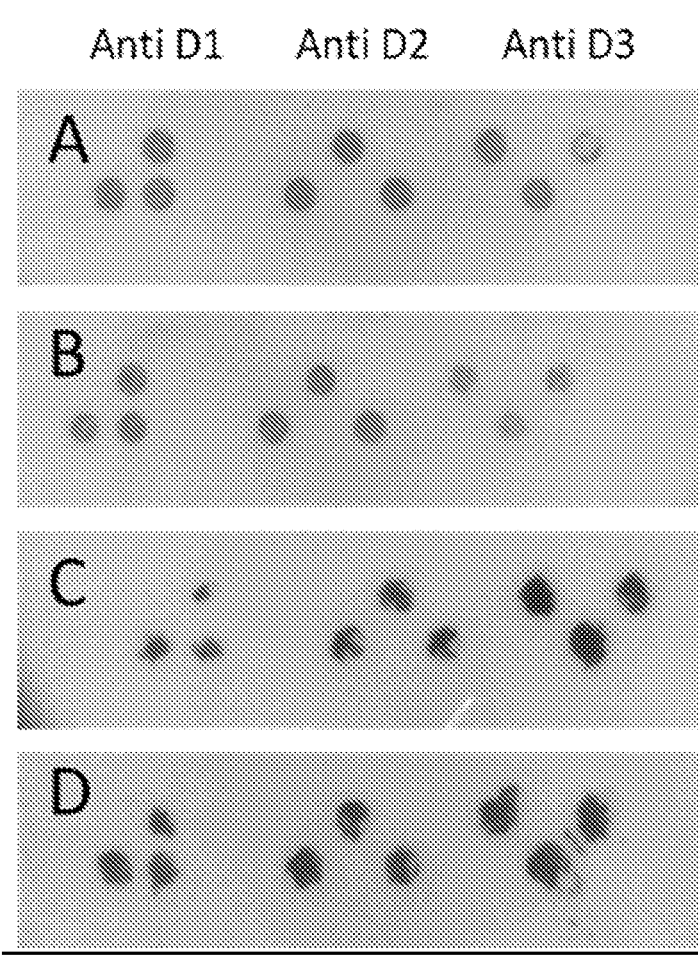

METHOD FOR CAPTURING AND IDENTIFYING CELLULAR AGGLUTINATES FOR DETECTING MULTIPLEX ANTI-ERYTHROCYTE ANTIBODIES

TECHNICAL FIELD

The present invention relates to the field of in vitro detection and diagnosis methods using in particular samples of biological origin. The methods more particularly involved relate to the detection of anti-erythrocyte antibodies which participate in blood group determination. The detection of anti-erythrocyte antibodies in biological samples remains of primary importance, in particular in immunohematology, in the blood transfusion field, and most particularly for determining blood groups or evaluating the risk in the recipient.

Testing for anti-erythrocyte antibodies encompasses, in clinical practice, a large number of antibodies referred to as regular or irregular, generally directed against antigenic motifs expressed at the surface of erythrocyte cells.

ABO blood group-related antigens are oligosaccharide motifs. The objective of ABO grouping is thus to determine four blood groups according to the presence or absence of two antigens, A and B, at the surface of red blood cells. Each individual is alternatively group A if possessing the A motif, group B if possessing the B motif, group AB if possessing the A and B motifs, and group O if possessing neither of the two motifs A or B.

Furthermore, each patient has, in their serum or plasma, the antibody or antibodies corresponding to the antigens that they do not have ("Landsteiner's" law). A group A subject carrying the A antigen has anti-B antibodies. A B subject carrying the B antigen has anti-A antibodies. An AB subject carrying the A and B antigens has neither anti-A antibodies nor anti-B antibodies. A group O subject carrying no A or B antigen has anti-A and anti-B antigens.

The consequences of an erroneous detection of anti-A or anti-B anti-erythrocyte antibodies are major, in the same way as a poor definition of the ABO group. This is because, if the anti-A (or anti-B) antibodies of the recipient were to bind to the A (or B) antigens of the donor's red blood cells, they would cause agglutination of these cells, or even their destruction. This agglutination would lead to the failure of the transfusion, and in certain cases, serious, or even dramatic, clinical reactions possibly resulting in the death of the patient concerned. For this reason, when a blood transfusion is to be carried out, the compatibility between blood groups must absolutely be respected.

The reliability requirements relating to tests of this type are therefore extreme. The Order of Apr. 26, 2002 amending the order of Nov. 26, 1999 relating to the correct execution of medical biology analyses, published in the Journal Officiel de la République Française (JORF) [Official Journal of the French Republic], stipulates that the performance of ABO blood grouping is based on two complementary tests:

a cell-based test, referred to as Beth-Vincent tests, consisting in testing for A (ABO1) and B (ABO2) antigens with the following monoclonal reagents: anti-A (anti-ABO1), anti-B (anti-ABO2) and anti-AB (anti-ABO3);

a plasma (serum) test, referred to as Simonin test or Simonin-Michon test, consisting in testing for anti-A and anti-B antibodies with A1 and B test red blood cells, it being obligatory for at least one of these red blood cells to be of Rhesus (RH) negative phenotype.

It is the consistency of these tests which determines the ABO group of the patient.

Other anti-erythrocyte antibodies are also involved in transfusion safety; they recognize: Rhesus, Kell, MNS, P, Lutheran, lewis, Duffy, Kidd, Diego, Cartwright, Xg, Scianna, Dombrock, Colton, Landsteiner-Wiener, Chido/Rodgers, Hh, Kx, Gerbich, Cromer, Knops, Indian, OK, RAPH, John Milton Hagen, Li, Globoside, GIL, Rh-associated glycoprotein, Forssmann, JR, LAN, VEL, CD59.

Outside of pathological situations, such as autoimmune diseases, the serum of an individual can contain antibodies directed against one or more of the antigens listed above. These antibodies appear when there is antigenic stimulation by foreign red blood cells, for example following immunization against one or more antigens during a blood transfusion or else during a pregnancy by material immune reaction directed against the fetal red blood cell antigens not belonging to the maternal group, in particular during birth. These antibodies termed "irregular" (or "immune") are usually of IgG isotype.

The testing for these "irregular" antibodies is called an irregular agglutinin test (RAI), an indirect Coombs test or an indirect antiglobulin test (TIA). These tests are aimed at detecting the presence of antibodies directed against foreign erythrocyte markers. These tests are based on the agglutination of test red blood cells, the phenotypes of which are known, by the patient's plasma and after addition of anti-human globulin. Numerous types of red blood cells are therefore used in the tests. Comparison of the results makes it possible to deduce the specificity or the specificities of the antibodies.

In a transfusion context, the objective will be to assign to the patients the red blood cell pellets having the best compatibility.

PRIOR ART

Testing for anti-erythrocyte antibodies in immunohematology is based on the agglutination of test red blood cells, the phenotype of which is known. There are a large number of variants of these techniques. They can be manual, on an opaline plate, in a tube or in a microplate well, in a gel column, or completely automated. Although these tests are very efficient, they have not significantly evolved for 60 years and have certain limits:

the final result corresponds to the cumulation of several single results obtained for each antibody tested, numerous tests must be repeated, which requires exemplary traceability;

the multiplication of the tests leads to an extension of the times taken to obtain results;

the multiplication of the tests requires recourse to different taking of samples, which can influence the reliability of the test and requires a large volume of blood, which can be a problem in certain patients (for example infants and highly anemic patients).

Nevertheless, many laboratories/companies have tried to miniaturize and combine the tests to be carried out. However, the results obtained by these techniques are difficult to correlate to the conventional techniques.

WO85/01354 and WO02/16942 teach a method for detecting antibodies in the blood, comprising a step of adsorption of an antigen on a solid surface.

EP0223978A1 teaches a device for determining a blood group, consisting of a solid substrate and of one or more antibodies which react with red blood antigenic determinants.

US2007077605 teaches an optical device of biodisk type, for determining a blood group.

WO2007/051844A1 and WO2008148886A1 teach devices or methods for identifying anti-erythrocyte antibodies in a sample, comprising bringing into contact with groups of beads or particles.

WO2009007649A1 teaches a device for determining a blood group, comprising a support including a reactive zone consisting of a porous membrane and of an absorbent membrane.

WO2012010666 teaches a method for detecting anti-erythrocyte antibodies, comprising bringing a sample into contact with magnetic particles bearing said erythrocytes.

WO2019158726A1 teaches a detection device consisting of a support and of a hydrophobic porous membrane comprising beads complexed with an antibody or an antigen.

DISCLOSURE OF THE INVENTION

There is a need to develop new methods for the detection of anti-erythrocyte antibodies. In particular, there is a need to develop new methods which remain applicable in clinics, in blood banks and in medical test laboratories.

There also remains a need to develop methods that can be adapted to automated high-throughput techniques, more particularly methods which allow the multiplex detection of anti-erythrocyte antibodies.

There also remains a need to develop methods which are acceptable in terms of the regulatory requirements in medical biology and most particularly which meet the requirements of a plasma test of "Simonin" type or RAI (irregular agglutinin test) type.

The invention is precisely aimed at meeting all of these needs.

SUMMARY OF THE INVENTION

To meet these needs, the inventors propose to take advantage of the fact that antibody biochips can be advantageously used as an agglutinated-cell sorting system.

In particular, the originality of this approach is based on the fact that the capture of agglutinated cells on antibody deposits is able to produce a stronger signal having a different morphology than that generated by non-agglutinated cells.

Knowing the nature of the antibodies deposited, in particular monoclonal antibodies, on the support, and also their specificity with respect to the antigens of interest, the inventors have been able to determine the cell phenotypes involved in the agglutination and therefore the nature of the antibodies initially present in the sample tested.

This technology can be advantageously used in the context of the testing for regular anti-erythrocyte antibodies such as anti-group ABO antibodies, or irregular anti-erythrocyte antibodies. This application is of most particular advantage for carrying out the indirect plasma tests or Simonin test and carrying out an irregular agglutinin test (RAI).

Surprisingly, the inventors thus demonstrate that this method has a reliability that is at least comparable to the gel column tests usually implemented in immunohematology, while at the same time remaining compatible with multiplex applications.

Such multiplex applications can comprise or consist, in particular, of the detection:
- of several types of anti-erythrocyte antibodies in a sample;
- of several types of anti-erythrocyte antibodies in several samples.

Advantageously, these applications can therefore allow the simultaneous detection of several parameters, in one or more samples.

Thus, according to its main aspect, the present invention relates to an in vitro method for detecting anti-erythrocyte antibodies in a sample, comprising at least the following steps:
- a) bringing said sample into contact with one or more test erythrocyte(s) or a suspension of one or more test erythrocyte(s) of known phenotype, under conditions capable of inducing hemagglutination, so as to obtain a reaction mixture;
- b) bringing said reaction mixture into contact with a solid support containing a plurality of defined adsorption zones which have previously bonded antibodies or antibody fragments capable of binding antigenic determinants present on said test erythrocyte(s);
- c) determining the presence or absence of a hemagglutination reaction on at least one of said adsorption zones, so as to detect the presence or absence of anti-erythrocyte antibodies in said sample;
- said steps a) and b) being carried out separately or simultaneously.

In particular, the in vitro detection method according to the invention can be characterized in that said anti-erythrocyte antibodies to be detected are capable of specifically binding antigenic determinants chosen from the following systems or antigens: ABO, Rhesus, Kell, MNS, P, Lutheran, lewis, Duffy, Kidd, Diego, Cartwright, Xg, Scianna, Dombrock, Colton, Landsteiner-Wiener, Chido/Rodgers, Hh, Kx, Gerbich, Cromer, Knops, Indian, OK, RAPH, John Milton Hagen, Li, Globoside, GIL, Rh-associated glycoprotein, Forssmann, JR, LAN, VEL, CD59.

In particular, the in vitro detection method according to the invention can be characterized in that said anti-erythrocyte antibodies to be detected are capable of specifically binding antigenic determinants of the ABO system.

In particular, the in vitro detection method according to the invention can be characterized in that said antibodies or antibody fragments of the adsorption zone are monoclonal or polyclonal antibodies chosen from: anti-A antibodies (ABO1), anti-B antibodies (ABO2), anti-AB antibodies (ABO3), anti-H antibodies (H1), anti-D antibodies (RH1), anti-C antibodies (RH2), anti-c antibodies (RH4), anti-E antibodies (RH3), anti-e antibodies (RH5), anti-K antibodies (KEL1), anti-k antibodies (KEL2), anti-Kpb antibodies (KEL4), anti-Fya antibodies (FY1), anti-Fyb antibodies (FY2), anti-Jka antibodies (JK1), anti-Jkb antibodies (JK2), anti-S antibodies (MNS3), anti-s antibodies (MNS4), anti-Lea antibodies (LE1), anti-Leb antibodies (LE2), anti-M antibodies (MNS1), anti-N antibodies (MNS2), anti-P1 antibodies, anti-Kpa antibodies (KEL3), anti-Lua antibodies (LU1), anti-Lub antibodies (LU2), anti-Cw antibodies (RH8).

In particular, the in vitro detection method according to the invention can be characterized in that at least two of the adsorption zones of the solid support each bond a plurality of antibodies or antibody fragment(s) capable of binding a distinct erythrocyte antigenic determinant.

In particular, the in vitro detection method according to the invention can be characterized in that the sample is a biological sample chosen from: a human serum, a human plasma and a human whole blood sample.

In particular, the in vitro detection method according to the invention can be characterized in that at least two of the adsorption zones of the solid support are at least 100 μm apart from one another, and/or that said adsorption zones define an area of at least 10000 μm².

In particular, the in vitro detection method according to the invention can be characterized in that said solid support is a plastic support, and said adsorption zones are hydrophilic.

According to one embodiment, the in vitro detection method according to the invention can be characterized in that said plurality of defined absorption zones forms a wall that is inclined relative to the rest of all or part of said solid support; for example, which comprises an inclined plane that forms an angle with a horizontal plane consisting of all or part of said solid support, and in particular an angle with a horizontal plane consisting of all or part of a zone of said solid support which does not bond antibodies and/or antibody fragment(s).

According to certain embodiments, the in vitro detection method according to the invention can be characterized in that said plurality of defined absorption zones is planar, conical or hemispherical.

In particular, the in vitro detection method according to the invention can be characterized in that the antibodies or antibody fragments capable of binding the antigenic determinants are noncovalently bonded to the defined adsorption zones.

According to certain particular embodiments, the in vitro detection method according to the invention can be characterized in that the adsorption zones of the solid support are, at least partly, functionalized with one or more bonding polymers comprising a polysaccharide backbone provided with:

aromatic groups of the form —X—CONH-Z, where X represents a linear or branched, substituted or unsubstituted alkyl chain comprising from 1 to 6 carbon atoms, and Z represents an aryl function; and/or carboxylic acid groups of the form —X—COOH, where X represents a linear or branched, substituted or unsubstituted alkyl chain comprising from 1 to 6 carbon atoms.

According to certain particular embodiments, the in vitro detection method according to the invention can be characterized in that said solid support is, at least partly, functionalized with one or more bonding polymers comprising one or more groups that are positively charged at the pH of said reaction mixture.

In particular, the in vitro detection method according to the invention can be characterized in that the presence or absence of a hemagglutination reaction on said adsorption zone(s) is determined by comparison with a reference zone different than said zone(s) of said solid support.

In particular, the in vitro detection method according to the invention can be characterized in that the determination step c) is carried out after a step of sedimenting said reaction mixture on said solid support.

In particular, the in vitro detection method according to the invention can be characterized in that the determination step c) is carried out after a step of centrifuging said solid support.

The invention is described in greater detail below.

DESCRIPTION OF THE FIGURES

FIG. 1: illustration of the general principle of the invention, applied to the determination of anti-erythrocyte antibodies in a sample.

FIG. 2: illustration of a plan of a biotube/plate, or array of deposits, including at the bottom of wells one or more spots (or defined adsorption zones), consisting of anti-ABO and 3 anti-D antibodies. Spot A represents a deposit of anti-ABO1. Spot B represents a deposit of anti-ABO2. Spot D1 represents a deposit of anti-D. Spot D2 represents a deposit of anti-D. Spot D3 represents a deposit of anti-D.

FIG. 3: photographic images of the bottom of wells in the presence of human plasma samples. In 3A, result of a test starting from a sample AB. In 3B, result of a test starting from a sample A. In 3C, result of a test starting from a sample B. In 3D, result of a test starting from a sample O.

FIG. 4: photographic images of the bottom of wells in the presence of human plasma samples. In 4A, result of a test starting from a negative irregular sample. In 4B, result of a test starting from a negative irregular sample. In 4C, result of a test starting from a positive irregular sample. In 4D, result of a test starting from a positive irregular sample.

DETAILED DESCRIPTION

General Definitions

The term "plurality", such as "plurality of adsorption zones", implies the presence of "at least two"; this term can therefore, for example, denote 2, 3, 4, 5, 6, 7, 8, 9, 10, or even more than 10.

The terms "erythrocyte", "hematite" or "red blood cell" are used without distinction herein. The term "antigenic determinant present on the erythrocytes" encompasses not only any antigenic determinant physiologically present at the surface of erythrocytes, in particular any blood group determinant, but also any other determinant present at the surface of said erythrocytes, in particular which is non-physiological, and/or which is the result of immunological reactions, which are the result of innate or acquired immunity, such as antibodies, or antibody fragments, or elements belonging to the complement system.

The term "sample", in particular used to denote a biological sample, encompasses in particular any sample that may have been obtained beforehand from an individual, which includes any body fluid or body fluid fraction, or tissue biopsy, which may include erythrocytes and/or anti-erythrocyte antibodies, which may be physiological or pathological, and regular or irregular. Most particularly, a "biological sample" can denote herein any blood sample, or blood sample pellet, and/or any other blood-derived preparation, such as a whole blood sample, serum or plasma, lymph or cerebrospinal fluid. A sample may also include a saliva, sweat, tear, milk or urine sample.

The term "antibody or antibody fragment" encompasses all molecules of immunoglobulin type, and also any immunologically active portion of said immunoglobulins, such as the molecules containing one or more sites of interaction with an antigen specific for said immunoglobulins. In this respect, this term is not only limited to regular (natural) or irregular whole antibodies, but also encompasses antibody fragments and synthetic or recombinant variants thereof. Unless otherwise indicated, this term therefore encompasses equally "natural" and "unnatural" or synthetic antibodies obtained recombinantly or nonrecombinantly. Antibodies are conventionally defined by two heavy chains linked together by a disulfide bridge, and each heavy chain is itself linked to a light chain by one or more disulfide bridges. Unless otherwise indicated, this term therefore encompasses all the antibodies, or fragments of said antibodies, comprising one of the five main classes of heavy chain, chosen from IgM, IgD, IgG, IgA and IgE; or else one of the two types of light chain chosen from the lambda (l) and kappa (k) chains.

The term "synthetic antibody" encompasses all of the antibodies obtained in vitro and comprising at least one fragment of a variable region of an antibody. The synthetic antibodies can thus be chosen from the following constructs: Fab, a F(ab)'2, single domain antibody (sdAb), ScFv, Fab-scFv, ScFv-Fc, Sc(Fv)2, diabody, di-diabody, triabody, tetrabody, pentabody, unibody, minibody, maxibody, nanobody, Small Modular Immunopharmaceutical (SMIP), and the fragments comprising variable regions such as light variable (VL) and heavy variable (HL) chains.

The term "anti-erythrocyte antibody" denotes herein a regular or irregular antibody directed against at least one antigenic determinant present on erythrocytes.

The term "regular antibody" or "natural antibody" denotes herein any anti-erythrocyte antibody that may be naturally present in an individual, and therefore other than during any pathological condition and exposure to an outside antigen. This type of antibody generally encompasses all the ABO antibodies (for example anti-A and anti-B) and H antibodies.

The term "irregular antibody" denotes herein any anti-erythrocyte antibody which is not systematically present in subjects lacking the corresponding antigen. Generally, most non-ABO antibodies are conventionally defined as irregular antibodies, which includes in particular the following antibodies: anti-D, anti-C, anti-E, anti-c, anti-e, anti-K, anti-k, anti-Cw, anti-Kpa, anti-Kpb, anti-Fya, anti-Fyb, anti-Jka, anti-Jkb, anti-Lea, anti-Leb, anti-M, anti-N, anti-S, anti-s, anti-Lua, anti-Lub.

The term "hemagglutination" denotes, in its usual meaning, all the agglutination reactions comprising the binding of anti-erythrocyte antibodies to antigenic structures present at the surface of red blood cells, and capable of directly or indirectly leading to the formation of a red blood cell aggregate. This term therefore equally encompasses direct, indirect and passive hemagglutination reactions.

Methods

Thus, according to its main aspect, the present invention relates to an in vitro method for detecting anti-erythrocyte antibodies in a sample, comprising at least the following steps:

a) bringing said sample into contact with one or more test erythrocyte(s) or a suspension of one or more test erythrocyte(s) of known phenotype, under conditions capable of inducing hemagglutination, so as to obtain a reaction mixture;

b) bringing said reaction mixture into contact with a solid support containing a plurality of defined adsorption zones which have previously bonded antibodies or antibody fragments capable of binding antigenic determinants present on said test erythrocyte(s);

c) determining the presence or absence of a hemagglutination reaction on at least one of said adsorption zones, so as to detect the presence or absence of anti-erythrocyte antibodies in said sample;

said steps a) and b) being carried out separately or simultaneously.

According to one embodiment, steps a) and b) are carried out separately.

According to one embodiment, steps a) and b) are carried out simultaneously.

When steps a) and b) are carried out simultaneously, the in vitro detection method according to the invention can be characterized in that it comprises the following steps:

a) bringing (i) a solid support containing a plurality of defined adsorption zones which have previously bonded antibodies or antibody fragments capable of binding antigenic determinants present on test erythrocyte(s) into contact with (ii) a sample and (iii) one or more of said test erythrocyte(s) or a suspension of test erythrocyte(s) of known phenotype, under conditions capable of inducing hemagglutination; then b) determining the presence or absence of a hemagglutination reaction on at least one of said adsorption zones so as to detect the presence or absence of anti-erythrocyte antibodies in said sample.

The in vitro detection method according to the invention can be characterized in that said anti-erythrocyte antibodies to be detected are regular or irregular antibodies.

These antibodies are capable of specifically binding erythrocyte surface antigens.

In particular, the in vitro detection method according to the invention can be characterized in that said anti-erythrocyte antibodies to be detected are capable of specifically binding antigenic determinants chosen from the following systems or antigens: ABO, Rhesus, Kell, MNS, P, Lutheran, lewis, Duffy, Kidd, Diego, Cartwright, Xg, Scianna, Dombrock, Colton, Landsteiner-Wiener, Chido/Rodgers, Hh, Kx, Gerbich, Cromer, Knops, Indian, OK, RAPH, John Milton Hagen, Li, Globoside, GIL, Rh-associated glycoprotein, Forssmann, JR, LAN, VEL, CD59.

Thus, said anti-erythrocyte antibodies to be detected can be capable of specifically binding antigenic determinants chosen from the ABO and Rhesus systems or antigens.

Preferentially, said anti-erythrocyte antibodies to be detected are capable of specifically binding antigenic determinants of the ABO system.

Thus, said anti-erythrocyte antibodies to be detected may be anti-A antibodies, anti-B antibodies, or anti-H antibodies.

Most particularly, the antibodies that can be detected are "regular" antibodies.

According to certain embodiments, the anti-erythrocyte antibodies to be detected are chosen from IgM, IgD, IgG, IgA and IgE; in particular, chosen from IgM and IgG.

The biological sample can be in particular be any sample capable of containing anti-erythrocyte antibodies, and in particular any biological fluid, such as a blood sample, in particular a whole blood sample, or a blood derivative sample, such as plasma or serum, urine, cerebrospinal fluid, lymph, saliva, or a tissue sample, such as a tissue obtained by biopsy, a cell or a set of cells, or combinations thereof. A blood derivative denotes any product, in particular fluid product, obtained from a blood sample.

The sample to be analyzed may also be a culture medium and/or a culture supernatant. Before being analyzed, the sample may undergo one or more prior treatment steps, such as dilution, centrifugation, heat treatment and/or chemical treatment, cell lysis (for example due to one or more chaotropic agents, one or more reducing agents and/or due to heating), extraction, addition of an unlabeled detection ligand, or combinations thereof.

The sample may also be a mixture of at least two samples which may be of the same nature or of different nature, from one and the same individual or from different individuals. By way of example of a mixture of samples of different nature, mention may be made of a mixture of blood and serum, a mixture of blood and plasma, a mixture of serum and plasma, or else a mixture of blood, serum and plasma.

A preferred sample according to the invention is a blood and/or blood derivative sample or sample mixture.

In particular, the in vitro detection method according to the invention can be characterized in that the sample is a biological sample chosen from: a human serum, a human plasma, a human whole blood sample.

When the in vitro detection method according to the invention is carried out in a multiplex format, for example for the (simultaneous or non-simultaneous) analysis of several anti-erythrocyte antibodies, said method can involve a step of bringing a sample into contact with one or more test erythrocyte(s) or a suspension of test erythrocyte(s) of known phenotype.

According to one particular embodiment, the in vitro detection method according to the invention can thus be characterized in that it comprises at least the following steps:

a) bringing a sample into contact with one or more test erythrocyte(s) or a suspension of test erythrocyte(s) of known phenotype, under conditions capable of inducing hemagglutination so as to obtain a reaction mixture;

b) bringing said reaction mixture into contact with a solid support containing a plurality of defined adsorption zones which have previously bonded antibodies or antibody fragments capable of binding to antigenic determinants present on said test erythrocyte(s);

c) determining the presence or absence of a hemagglutination reaction on the adsorption zones brought into contact with said sample, so as to detect the presence or absence of the anti-erythrocyte antibodies in said sample;

said steps a) and b) being carried out separately or simultaneously.

In particular, the in vitro detection method according to the invention can be characterized in that the presence or absence of a hemagglutination reaction on said adsorption zone(s) is determined by comparison with a reference zone distinct from said solid support. According to certain embodiments, said reference zone distinct from said solid support can comprise or consist of a distinct defined adsorption zone, and/or a distinct compartment, and/or a distinct spot.

In particular, the in vitro detection method according to the invention can be characterized in that the determination step is carried out after a step of sedimenting said reaction mixture on said solid support.

In particular, the in vitro detection method according to the invention can be characterized in that the determination step is carried out after a step of centrifuging said solid support.

The in vitro detection methods according to the invention are particularly suitable for carrying out the Simonin test, and in particular in the form of multiplex methods.

According to these particular embodiments, the in vitro detection methods according to the invention are particularly suitable for detecting anti-erythrocyte antibodies, and in particular antibodies directed against antigenic determinants of the ABO system.

According to these particular embodiments, the antibodies bonded to the defined adsorption zones of the solid support are in particular chosen from anti-A antibodies (ABO1), anti-B antibodies (ABO2), anti-AB antibodies (ABO3); the test erythrocytes of known phenotype are in particularly chosen from erythrocytes expressing the antigenic determinants A1 and B.

In particular, in the context of the implementation of the Simonin test, said test erythrocyte(s) are of known or determinable Rhesus phenotype.

According to certain embodiments, all or some of these test erythrocyte(s) is (are) of Rhesus negative phenotype. Thus, according to some of these embodiments, at least one of these test erythrocyte(s) is of Rhesus (D) negative phenotype.

Preferentially, in the context of the implementation of the Simonin test, the solid support suitable for the invention comprises at least two defined adsorption zones each bonding antibodies or antibody fragments capable of binding distinct erythrocyte antigenic determinants.

Variants of the solid support that may be used in the detection methods are developed below.

Supports Used in the Methods

A solid support suitable for carrying out an in vitro method according to the invention contains a plurality of defined adsorption zones, said adsorption zones bonding antibodies or antibody fragments capable of binding erythrocyte antigenic determinants.

A solid support most particularly suitable for the invention is a solid support of multiplex type, that is to say a support capable of detecting one or more anti-erythrocyte antibodies (for example two, three, four, five, six, seven, eight, nine, ten, eleven, twelve, thirteen, fourteen, fifteen or more than fifteen), on one or more samples as described in the present application, simultaneously or non-simultaneously, during a multiplex analysis method.

Such a solid support can in particular be in the form of a plate, a microplate, a slide, beads, a membrane or a strip having several wells or a single well. Preferably, such a solid support can be placed in the form of a microplate or a strip having several wells or a single well.

A solid support can be made of any material suitable for carrying out the analysis method, such as a plastic support or a support other than plastic.

Such a solid support is for example a support based on a polymer or a polymer blend. A solid support suitable according to the invention is, for example, a support made of polystyrene, polypropylene, poly(meth)acrylate, polybutadiene or combinations thereof. Preferably, a suitable solid support is based on polystyrene, such as: an optionally breakable, COSTAR high binding microplate, or any other optionally breakable polystyrene microplate with a high binding capacity.

Another type of solid support suitable according to the invention is for example an inorganic support, such as glass, and/or a metal support.

Another example of a suitable solid support is a membrane, for example a membrane made of nitrocellulose, PVDF (polyvinylidene fluoride) or nylon, or combinations thereof.

According to one embodiment, a solid support suitable for the method comprises a single compartment. Said single compartment may be a compartment comprising one or more walls. Alternatively, said single compartment may be devoid of walls, and can then be likened to the solid support itself. The base of the compartment can then consist of the upper face of the solid support. An example of such a solid support comprising a single compartment optionally comprising one or more walls is a slide or a membrane.

Alternatively, said single compartment may be devoid of walls while at the same time being separated from the other compartments by a zone which makes it possible to avoid mixing between two adjacent samples, for example a hydrophobic zone.

In one particular embodiment of the invention, where a solid support (for example a slide or a membrane) comprises a single compartment, typically at least one (for example one or two) solid support is used per sample to be analyzed.

According to one embodiment, a solid support suitable for the method comprises a plurality of compartments.

When a solid support comprises at least two compartments, said compartments may be isolated from one another, so that they do not communicate between them, or have limited communication, that is to say so that the various compositions or solutions used for the analysis cannot circulate from one compartment to another during the analysis, or at least not freely.

Thus, according to one embodiment of said solid support, a solution (for example a sample) added to a compartment will not go into the other compartments, or will go in a limited manner For example, the compartment(s) comprise or consist of a base and one or more walls, said wall(s) isolating the compartment(s) from one another so that they do not communicate with one another.

An example of a compartment is a well.

A solid support comprises for example a plurality of wells, that is to say, for example, a set of at least two wells.

A solid support is for example a microplate.

The microplate may be a 96-well or 384-well microplate.

A solid support suitable for the method comprises a plurality of defined adsorption zones.

Said defined adsorption zones can in particular comprise, or even consist of, spots.

A defined adsorption zone does not necessarily have a single defined shape. In this respect, a defined adsorption zone may thus comprise one or more spots, evenly or unevenly spaced apart, and comprising at least one antibody or antibody fragment, capable of binding antigenic determinants of erythrocytes, bound to the surface of said support, and/or where appropriate of said compartment, in particular by noncovalent physicochemical interactions (in particular of weak, for example ionic, van der Waals, hydrogen and/or hydrophobic bond type) and/or via covalent bonds.

Nonexhaustively, the defined adsorption zones of the solid support, in particular the deposits of antibodies or antibody fragments, can be obtained manually or using any device, in particular any device capable of preparing microarrays, such as a contact device or contactless device, in particular any device which makes it possible to deposit volumes smaller than a microliter, such as piezoelectric or solenoid valve systems.

The term "spot" denotes herein a defined adsorption zone, or a portion of a defined adsorption zone of the solid support, for example of a compartment of the solid support, comprising at least said compound of interest bound to the surface of said solid support (or even, where appropriate, of said compartment), in particular by noncovalent physicochemical interactions (in particular of weak, for example ionic, van der Waals, hydrogen and/or hydrophobic bond type) and/or via covalent bonds, generally obtained by depositing at least one drop of a solution containing a given amount of said compound(s) of interest at a precise place at the surface of said support and/or of said compartment.

A spot may be discoidal or cylindrical in shape, or approximately discoidal or cylindrical in shape, for example oval, in particular when a solid support is a microplate or a slide. Alternatively, a spot may be square or rectangular in shape (this may in particular be a strip), for example when a solid support is a membrane, or any other shape.

A solid support can thus comprise at least two, or even three, defined adsorption zones, for example three zones, four zones or five zones, or at least six zones.

A solid support can thus comprise at least three spots, for example three spots, four spots or five spots, or at least six spots.

According to one embodiment, said antibodies or antibody fragments of the adsorption zone are monoclonal or polyclonal antibodies chosen from: anti-A antibodies (ABO1), anti-B antibodies (ABO2), anti-AB antibodies (ABO3), anti-H antibodies (H1), anti-D antibodies (RH1), anti-C antibodies (RH2), anti-c antibodies (RH4), anti-E antibodies (RH3), anti-e antibodies (RH5), anti-K antibodies (KEL1), anti-k antibodies (KEL2), anti-Kpb antibodies (KEL4), anti-Fya antibodies (FY1), anti-Fyb antibodies (FY2), anti-Jka antibodies (JK1), anti-Jkb antibodies (JK2), anti-S antibodies (MNS3), anti-s antibodies (MNS4), anti-Lea antibodies (LE1), anti-Leb antibodies (LE2), anti-M antibodies (MNS1), anti-N antibodies (MNS2), anti-P1 antibodies, anti-Kpa antibodies (KEL3), anti-Lua antibodies (LU1), anti-Lub antibodies (LU2), anti-Cw antibodies (RH8).

According to one embodiment, said antibodies or antibody fragments of the adsorption zone are monoclonal or polyclonal antibodies chosen from: anti-A antibodies (ABO1), anti-B antibodies (ABO2), anti-AB antibodies (ABO3), anti-D antibodies (RH1), anti-C antibodies (RH2), anti-c antibodies (RH4), anti-E antibodies (RH3), anti-e antibodies (RH5), anti-K antibodies (KEL1), anti-k antibodies (KEL2), anti-Kpb antibodies (KEL4), anti-Fya antibodies (FY1), anti-Fyb antibodies (FY2), anti-Jka antibodies (JK1), anti-Jkb antibodies (JK2), anti-S antibodies (MNS3), anti-s antibodies (MNS4), anti-Lea antibodies (LE1), anti-Leb antibodies (LE2), anti-M antibodies (MNS1), anti-N antibodies (MNS2), anti-P1 antibodies, anti-Kpa antibodies (KEL3), anti-Lua antibodies (LU1), anti-Lub antibodies (LU2), anti-Cw antibodies (RH8).

Such antibodies or antibody fragments of the adsorption zone are for example monoclonal or polyclonal antibodies, such as those that may be available to purchase from Diagast, Merck, Quotient or Biorad, and chosen from:
   anti-A monoclonal antibodies (ABO1), anti-B monoclonal antibodies (ABO2), anti-AB monoclonal antibodies (ABO3) which would be murine IgMs,
   anti-N monoclonal antibodies (MNS2) which would be murine IgGs,
   anti-D monoclonal antibodies (RH1), anti-C monoclonal antibodies (RH2), anti-c monoclonal antibodies (RH4), anti-E monoclonal antibodies (RH3), anti-e monoclonal antibodies (RH5), anti-Cw antibodies (RH8), anti-K monoclonal antibodies (KEL1), anti-Jka monoclonal antibodies (JK1), anti-Jkb monoclonal antibodies (JK2), anti-S monoclonal antibodies (MNS3), anti-s monoclonal antibodies (MNS4), anti-P1 monoclonal antibodies which would be human IgMs,
   anti-D monoclonal antibodies (RH1), anti-k monoclonal antibodies (KEL2), anti-Fya monoclonal antibodies (FY1), anti-M monoclonal antibodies (MNS1) which would be human IgGs,
   anti-Kpb antibodies (KEL4), anti-Kpa antibodies (KEL3), anti-Lua antibodies (LU1), anti-Lub antibodies (LU2), anti-Fyb antibodies (FY2), anti-Lea antibodies (LE1), anti-Leb antibodies (LE2).

According to one embodiment, at least two of the adsorption zones of the solid support each bond a plurality of antibodies and/or antibody fragment(s) capable of binding a distinct erythrocyte antigenic determinant.

According to one embodiment, at least two of the defined adsorption zones (for example of the spots) comprising said antibodies or antibody fragments of the solid support are at least 100 μm apart from one another, which can encompass in particular at least 200, 300, 400, 500, 600, 700, 800, 900 or 1000 μm.

According to certain embodiments, said adsorption zones define an area of at least 10000 μm², which can encompass in particular at least 100000, 20000, 30000, 40000 or 50000 μm².

According to certain embodiments, said adsorption zones comprise or consist of zones (in particular spots) with a maximum dimension (in particular diameter) of from 50 to 500 μm, which comprises 50, 60, 70, 80, 90, 100, 150, 200, 250, 300, 350, 400, 450 and 500 μm.

According to one embodiment, at least two of the adsorption zones of the solid support are at least 100 μm apart from one another, and/or said adsorption zones define an area of at least 10000 μm².

According to one embodiment, said adsorption zones are hydrophilic or hydrophobic.

According to one embodiment, said solid support is a plastic support, and said adsorption zones are hydrophilic.

According to one embodiment, the in vitro detection method according to the invention can be characterized in that said plurality of defined absorption zones forms a wall that is inclined relative to the rest of any or a portion of said solid support.

According to certain embodiments, the in vitro detection method according to the invention can be characterized in that said plurality of defined absorption zones is planar, conical or hemispherical.

According to one embodiment, the antibodies or antibody fragments capable of binding the antigenic determinants are covalently bonded to the defined adsorption zones.

According to one embodiment, the antibodies or antibody fragments capable of binding the antigenic determinants are noncovalently bonded to the defined adsorption zones.

According to certain particular embodiments, the adsorption zones of the solid support are, at least partly, functionalized with one or more bonding polymer(s), said bonding polymer(s) immobilizing said antibodies or antibody fragments capable of binding the antigenic determinants.

Thus, according to certain particular embodiments, the adsorption zones of the solid support are, at least partly, covalently or noncovalently functionalized with one or more bonding polymers.

Nonexhaustively, such bonding polymers may for example consist of bonding polymers mentioned in WO2012/052874.

Thus, according to certain embodiments, the adsorption zones of the solid support are, at least partly, functionalized with one or more bonding polymers comprising a polysaccharide backbone.

The term "polysaccharide backbone" as defined herein encompasses any structure formed by a set of sugars (or saccharide units), bonded together by saccharide bonds, in particular O-saccharide bonds. This polysaccharide backbone can in particular be linear or branched. According to certain embodiments, it comprises from 80 to 600 saccharide units, and in particular from 150 to 350 saccharide units.

According to certain embodiments, the adsorption zones of the solid support are, at least partly, functionalized with one or more bonding polymers comprising a polysaccharide backbone provided with aromatic groups and/or carboxylic acid groups, which may be substituted or unsubstituted.

According to certain embodiments, the adsorption zones of the solid support are, at least partly, functionalized with one or more bonding polymers comprising a polysaccharide backbone provided:

with aromatic groups of the form —X—CONH-Z, where X represents a substituted or unsubstituted, linear or branched alkyl chain comprising from 1 to 6 carbon atoms, and Z represents an aryl function; and/or with carboxylic acid groups of the form —X—COOH, where X represents a substituted or unsubstituted, linear or branched alkyl chain comprising from 1 to 6 carbon atoms.

According to certain particular embodiments, the adsorption zones of the solid support are, at least partly, functionalized with one or more bonding polymers bonded to said substrate (in particular to said defined adsorption zone) noncovalently, and comprising a polysaccharide backbone provided:

with aromatic groups of the form —X—CONH-Z, where X represents a substituted or unsubstituted, linear or branched alkyl chain comprising from 1 to 6 carbon atoms, and Z represents an aryl function; and/or with carboxylic acid groups of the form —X—COOH, where X represents a substituted or unsubstituted, linear or branched alkyl chain comprising from 1 to 6 carbon atoms.

According to certain particular embodiments, the adsorption zones of the solid support are, at least partly, functionalized with one or more bonding polymers bonded to said substrate (in particular to said defined adsorption zone) noncovalently, and comprising a polysaccharide backbone provided:

with aromatic groups of the form —X—CONH-Z, where X represents a substituted or unsubstituted, linear or branched alkyl chain comprising from 1 to 6 carbon atoms, and Z represents an aryl function; and/or with carboxylic acid groups of the form —X—COOH, where X represents a substituted or unsubstituted, linear or branched alkyl chain comprising from 1 to 6 carbon atoms; and said bonding polymer(s) immobilizing said antibodies or antibody fragments capable of binding said antigenic determinants.

According to certain embodiments, said solid support is, at least partly, functionalized with one or more bonding polymers comprising one or more groups that are positively charged at the pH of said reaction mixture.

Example of Preparation of the Plates and of Implementation of the Method for the Simonin Test Anti-A antibodies (ABO1) and anti-B antibodies (ABO2) were deposited at the bottom of the wells of microtitration plates so as to form a plurality of defined adsorption zones.

The samples (human plasmas) to be tested are brought into contact with test red blood cells in the wells. The wells containing the test red blood cells and the samples are then centrifuged for 2 min at 2000 g. At the end of centrifugation, the supernatant is removed and then the bottom of the wells is imaged.

The presence or absence of agglutination may be detected or not detected at each antibody deposit by visual analysis or by image analysis.

96 plasma samples were tested in the context of the anti-ABO antibody detection.

The simple visual analysis of the distribution of the agglutinates on the various antibodies shows a 100% correlation with the standard techniques.

Example of Preparation of the Plates and of Implementation of the Method for RAI Three different anti-D antibodies were deposited at the bottom of the wells of microtitration plates so as to form a plurality of defined adsorption zones. The samples (human plasmas) to be tested are brought into contact with one or more test red blood cells in source plate wells. The wells containing the test red blood cells and the samples are then centrifuged for 2 min at 800 g.

At the end of centrifugation, the supernatant is removed, and then two washes in PBS are carried out.

At the end of the final centrifugation, the supernatant is removed.

The resulting pellet is resuspended in LISS buffer. Before the deposit in the well of the biochip, anti-human globulin is added to this mixture.

The wells are then centrifuged for 2 min at 2000 g.

At the end of centrifugation, the supernatant is removed, washing with PBS-Tween (PBST) is carried out and then the bottom of the wells is imaged.

32 plasma samples were tested in the context of irregular antibody detection.

The simple visual analysis of the separation shows an 87% correlation with the standard techniques.

Materials & Methods.

Fabrication of Biochips

Anti-A antibodies (ABO1), anti-B antibodies (ABO2) and 3 anti-D antibodies, from culture media, were purified beforehand. Each well of a previously functionalized microtitration plate was imprinted with these antibodies diluted in PBS buffer.

A contactless depositing robot using piezoelectric technology with a depositing system generating drops of 500 pl is used. The plates are then dried using a thermo ventilator for 10 minutes at 80° C. and then directly saturated with 200 μl of a 5% milk solution in PBS for one hour at ambient temperature. The plates are then washed three times with 200 μl of PBS. The wells are finally emptied, and dried for 1 h at 37° C., before being packaged and sealed in the presence of a sachet of desiccant in an aluminum bag.

The plan of the biochips fabricated (or deposit array) at the bottom of each well of the microplates is shown in FIG. 2.

Detection of Regular Antibodies in Human Plasmas

For the test, 100 μl of undiluted human plasma are mixed with 50 μl of a corpuscle suspension containing 0.5% of corpuscles from an A patient (test red blood cells A) and 0.5% of corpuscles from a B patient (test red blood cells B). The mixture is transferred into a well in which antibodies have been previously deposited.

The plates are centrifuged for 2 minutes at 2000 g at 4° C.

The supernatant is removed and then a PBS washing step is carried out. The bottoms of the wells of the microtitration plate are then imaged.

Detection of Irregular Antibodies in Human Plasmas

For the test, 50 μl of undiluted human plasma are mixed with 40 μl of test red blood cells O at 0.8%. The mixture is incubated for 15 min at 37° C. and then centrifuged for 2 min at 800 g. The supernatant is removed. Twice in succession, the pellet is resuspended in 100 μl of PBS and centrifuged.

After the final centrifugation, the supernatant is removed and the red blood cells are resuspended in 60 μl of LISS buffer, to which mixture are added 60 μl of anti-human globulin.

This mixture is deposited in the wells of the biochip which is then centrifuged for 2 min at 2000 g.

The supernatant is removed, then the well is washed with 200 μl of PBST at 0.1%.

The bottoms of the wells of the microtitration plate are then imaged.

Results

Visual analysis of the results is possible by observing the photos of the well bottoms (FIG. 3). Homogeneous circular spots are observed in the defined adsorption zones. They show the absence of agglutination. Conversely, the presence of large agglutinates that are much greater than the size of the deposits of origin and very nonhomogeneous indicates a positive agglutination.

FIG. 3A corresponds to a photo of a biochip incubated in the presence of a sample from an AB patient. Homogeneous regular spots are observed on the anti-A and anti-B deposits, indicating the absence of agglutination.

FIG. 3B corresponds to a photo of a biochip incubated in the presence of a sample from an A patient. Homogeneous regular spots are observed on the anti-A deposits and irregular and very intense spots are observed on the anti-B deposits. This indicates the absence of agglutination of the test red blood cells A, but agglutination of the test red blood cells B.

FIG. 3C corresponds to a photo of a biochip incubated in the presence of a sample from a B patient. Homogeneous regular spots are observed on the anti-B deposits and irregular and very intense spots are observed on the anti-A deposits. This indicates the absence of agglutination of the test red blood cells B, but agglutination of the test red blood cells A.

FIG. 3D corresponds to a biochip incubated in the presence of a sample from an O patient. Only irregular and very intense spots are observed, both on the anti-A deposits but also on the anti-B deposits. This indicates agglutination of the test red blood cells A and B.

This analysis was carried out on 23 frozen plasma samples and showed an efficiency of 100% on the 96 samples tested.

Detection of Irregular Antibodies in Human Plasmas

Results

Visual analysis of the results is possible by observing the photos of the well bottoms (FIG. 4). Homogeneous circular spots are observed in the defined adsorption zones. They show the absence of agglutination. Conversely, the presence of large agglutinates that are much greater than the size of the deposits of origin and very nonhomogeneous and more intense indicates a positive agglutination.

FIG. 4A corresponds to a photo of a biochip incubated in the presence of a sample from a patient not having an irregular antibody. Homogeneous regular spots are observed on the anti-D deposits, indicating the absence of agglutination.

FIG. 4B corresponds to a photo of a biochip incubated in the presence of a second sample from a patient not having an irregular antibody. Homogeneous regular spots are observed on the anti-D deposits, indicating the absence of agglutination.

FIG. 4C corresponds to a photo of a biochip incubated in the presence of a sample from a patient having anti-K irregular antibodies. Irregular spots which are very intense are observed on the anti-D deposits. This indicates agglutination of the test red blood cells and therefore the presence of irregular antibodies.

FIG. 4D corresponds to a photo of a biochip incubated in the presence of a sample from a patient having anti-D irregular antibodies. Irregular spots which are very intense are observed on the anti-D deposits. This indicates agglutination of the test red blood cells and therefore the presence of irregular antibodies.

This analysis was carried out on 32 frozen plasma samples and showed an efficiency of 87% on the 32 samples tested.

The invention claimed is:

1. An in vitro method for detecting anti-erythrocyte antibodies in a sample, comprising at least the following steps:

a) bringing said sample containing anti-erythrocyte antibodies into contact with one or more test erythrocyte(s) or a suspension of test erythrocyte(s) of known phenotype, under conditions capable of inducing hemagglutination, so as to obtain a reaction mixture;

b) bringing said reaction mixture into contact with a solid support containing a plurality of defined adsorption zones which have previously bonded antibodies or antibody fragments capable of binding antigenic determinants present on said test erythrocyte(s), wherein at least two of the adsorption zones each bond a plurality of antibodies and/or antibody fragment(s) capable of binding a distinct erythrocyte antigenic determinant;

c) determining the presence or absence of a hemagglutination reaction on at least one of said adsorption zones, wherein the presence of a hemagglutination reaction indicates the presence of anti-erythrocyte antibodies from the sample which recognize the same antigenic determinants recognized by the previously bonded antibodies or antibody fragments and wherein the absence of a hemagglutination reaction indicates the absence of anti-erythrocyte antibodies from the sample which recognize the same antigenic determinants recognized by the previously bonded antibodies or antibody fragments;

said steps a) and b) being carried out separately or simultaneously.

2. The in vitro detection method as claimed in claim 1, wherein said anti-erythrocyte antibodies to be detected are capable of specifically binding antigenic determinants chosen from the following systems or antigens: ABO, Rhesus, Kell, MNS, P, Lutheran, lewis, Duffy, Kidd, Diego, Cartwright, Xg, Scianna, Dombrock, Colton, Landsteiner-Wiener, Chido/Rodgers, Hh, Kx, Gerbich, Cromer, Knops, Indian, OK, RAPH, John Milton Hagen, Li, Globoside, GIL, Rh-associated glycoprotein, Forssmann, JR, LAN, VEL, CD59.

3. The in vitro detection method as claimed in claim 1, wherein said anti-erythrocyte antibodies to be detected are capable of specifically binding antigenic determinants of the ABO system.

4. The in vitro detection method as claimed in claim 1, wherein said antibodies or antibody fragments of the adsorption zone are monoclonal or polyclonal antibodies chosen from: anti-A antibodies (ABO1), anti-B antibodies (ABO2), anti-AB antibodies (ABO3), anti-D antibodies (RH1), anti-C antibodies (RH2), anti-c antibodies (RH4), anti-E antibodies (RH3), anti-e antibodies (RH5), anti-K antibodies (KEL1), anti-k antibodies (KEL2), anti-Kpb antibodies (KEL4), anti-Fya antibodies (FY1), anti-Fyb antibodies (FY2), anti-Jka antibodies (JK1), anti-Jkb antibodies (JK2), anti-S antibodies (MNS3), anti-s antibodies (MNS4), anti- Lea antibodies (LE1), anti-Leb antibodies (LE2), anti-M antibodies (MNS1), anti-N antibodies (MNS2), anti-P1 antibodies, anti-Kpa antibodies (KEL3), anti-Lua antibodies (LU1), anti-Lub antibodies (LU2), anti-Cw antibodies (RH8).

5. The in vitro detection method as claimed in claim 1, wherein the sample is a biological sample chosen from: a human serum, a human plasma and a human whole blood sample.

6. The in vitro detection method as claimed in claim 1, wherein at least two of the adsorption zones of the solid support are at least 100 μm apart from one another, and/or that said adsorption zones define an area of at least 10000 $\mu m^2$.

7. The in vitro detection method as claimed in claim 1, wherein said solid support is a plastic support, and said adsorption zones are hydrophilic.

8. The in vitro detection method as claimed in claim 1, wherein said plurality of defined adsorption zones comprise a plane that is inclined relative to the rest of all or a portion of said solid support.

9. The in vitro detection method as claimed in claim 1, wherein the antibodies or antibody fragments capable of binding the antigenic determinants are noncovalently bonded to the defined adsorption zones.

10. The in vitro detection method as claimed in claim 1, wherein the adsorption zones of the solid support are functionalized with one or more bonding polymers comprising a polysaccharide backbone provided:

with aromatic groups of the form —X—CONH-Z, where X represents a substituted or unsubstituted, linear or branched alkyl chain comprising from 1 to 6 carbon atoms, and Z represents an aryl function; and/or with carboxylic acid groups of the form —X—COOH, where X represents a substituted or unsubstituted, linear or branched alkyl chain comprising from 1 to 6 carbon atoms.

11. The in vitro detection method as claimed in claim 1, wherein said solid support is functionalized with one or more bonding polymers comprising one or more groups that are positively charged at the pH of said reaction mixture.

12. The in vitro detection method as claimed in claim 1, wherein the presence or absence of a hemagglutination reaction on said adsorption zone is determined by comparison with a distinct reference zone of said solid support.

13. The in vitro detection method as claimed in claim 1, wherein the determining step c) is carried out after a step of sedimenting said reaction mixture on said solid support.

14. The in vitro detection method as claimed in claim 1, wherein the determining step c) is carried out after a step of centrifuging said solid support.

15. The in vitro detection method as claimed in claim 1, wherein the sample is a plasma sample.

* * * * *